(12) United States Patent
Mitsuya et al.

(10) Patent No.: US 11,337,590 B2
(45) Date of Patent: May 24, 2022

(54) ENDOSCOPE

(71) Applicant: OLYMPUS CORPORATION, Tokyo (JP)

(72) Inventors: Tae Mitsuya, Machida (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 522 days.

(21) Appl. No.: 16/392,841

(22) Filed: Apr. 24, 2019

(65) Prior Publication Data

US 2019/0246877 A1    Aug. 15, 2019

Related U.S. Application Data

(63) Continuation of application No. PCT/JP2017/036505, filed on Oct. 6, 2017.

(30) Foreign Application Priority Data

Oct. 25, 2016 (JP) .............................. JP2016-208875

(51) Int. Cl.
*A61B 1/005* (2006.01)
*A61B 1/012* (2006.01)
(Continued)

(52) U.S. Cl.
CPC ............ *A61B 1/0057* (2013.01); *A61B 1/005* (2013.01); *A61B 1/00066* (2013.01);
(Continued)

(58) Field of Classification Search
CPC ... A61B 1/0057; A61B 1/005; A61B 1/00066; A61B 1/0125; A61B 1/015; A61B 1/018; G02B 23/24
(Continued)

(56) References Cited

U.S. PATENT DOCUMENTS

| 2014/0200513 A1* | 7/2014 | Koitabashi ........... A61B 1/0055 |
| | | 604/95.04 |
| 2014/0359972 A1* | 12/2014 | Okada ................ A61B 1/00066 |
| | | 16/110.1 |
| 2015/0272425 A1* | 10/2015 | Ueda .................. A61B 1/00078 |
| | | 600/144 |

FOREIGN PATENT DOCUMENTS

| JP | 2003093330 A | 4/2003 |
| JP | 2003190078 A * | 7/2003 |

(Continued)

OTHER PUBLICATIONS

English translation of International Preliminary Report on Patentability dated May 9, 2019, together with the Written Opinion received in related International Application No. PCT/JP2017/036505.

(Continued)

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An endoscope includes a first pulling section, an first elongated member, a restricting portion, a sliding surface, and a partition. The restricting portion is provided inside the operation section, and is configured to restrict a position of the first pulling section. The sliding surface is provided in the restricting portion, and allows the first pulling section to move along the axial direction. The partition covers at least a part of the sliding surface and the first pulling section, and is configured to partition the first elongated member and the first pulling section. The partition and the restricting portion are configured to restrict a moving range of the connection portion within a range of the sliding surface.

15 Claims, 15 Drawing Sheets

(51) Int. Cl.
    *A61B 1/015*     (2006.01)
    *A61B 1/018*     (2006.01)
    *G02B 23/24*     (2006.01)
    *A61B 1/00*     (2006.01)

(52) U.S. Cl.
    CPC .............. *A61B 1/015* (2013.01); *A61B 1/018* (2013.01); *A61B 1/0125* (2013.01); *G02B 23/24* (2013.01)

(58) Field of Classification Search
    USPC ........................................................ 600/146
    See application file for complete search history.

(56) References Cited

FOREIGN PATENT DOCUMENTS

| | | |
|---|---|---|
| JP | 2003190078 A | 7/2003 |
| JP | 2012075709 A | 4/2012 |
| JP | 2014039611 A | 3/2014 |
| WO | 2014065092 A1 | 5/2014 |

OTHER PUBLICATIONS

International Search Report dated Dec. 26, 2017 issued in PCT/JP2017/036505.

\* cited by examiner

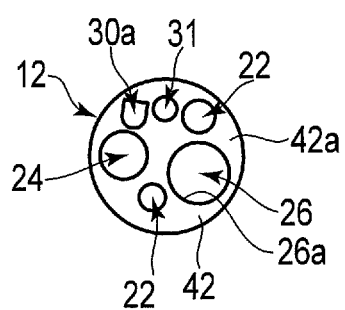
F I G. 1B

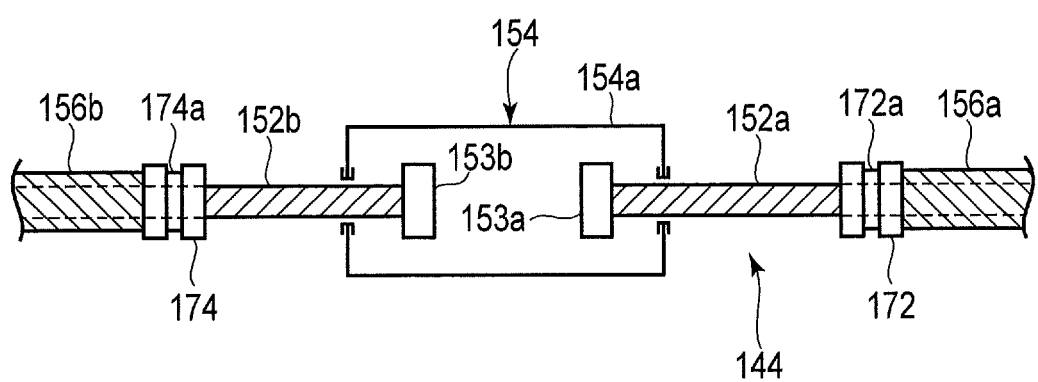
F I G. 3B

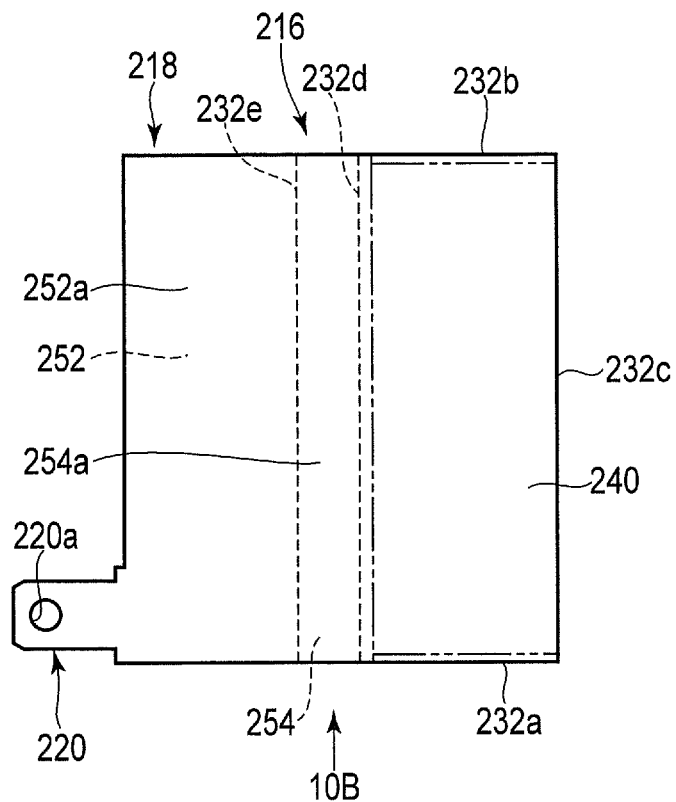
F I G. 10A
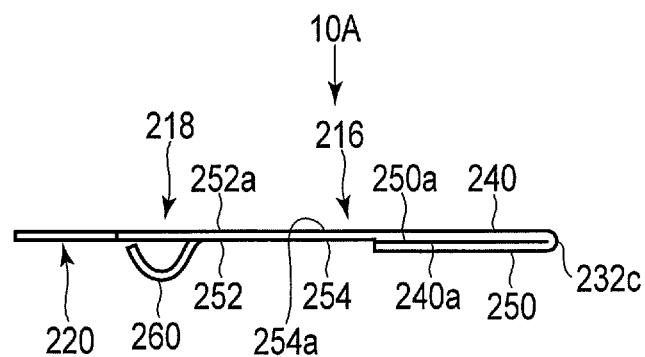
F I G. 10B

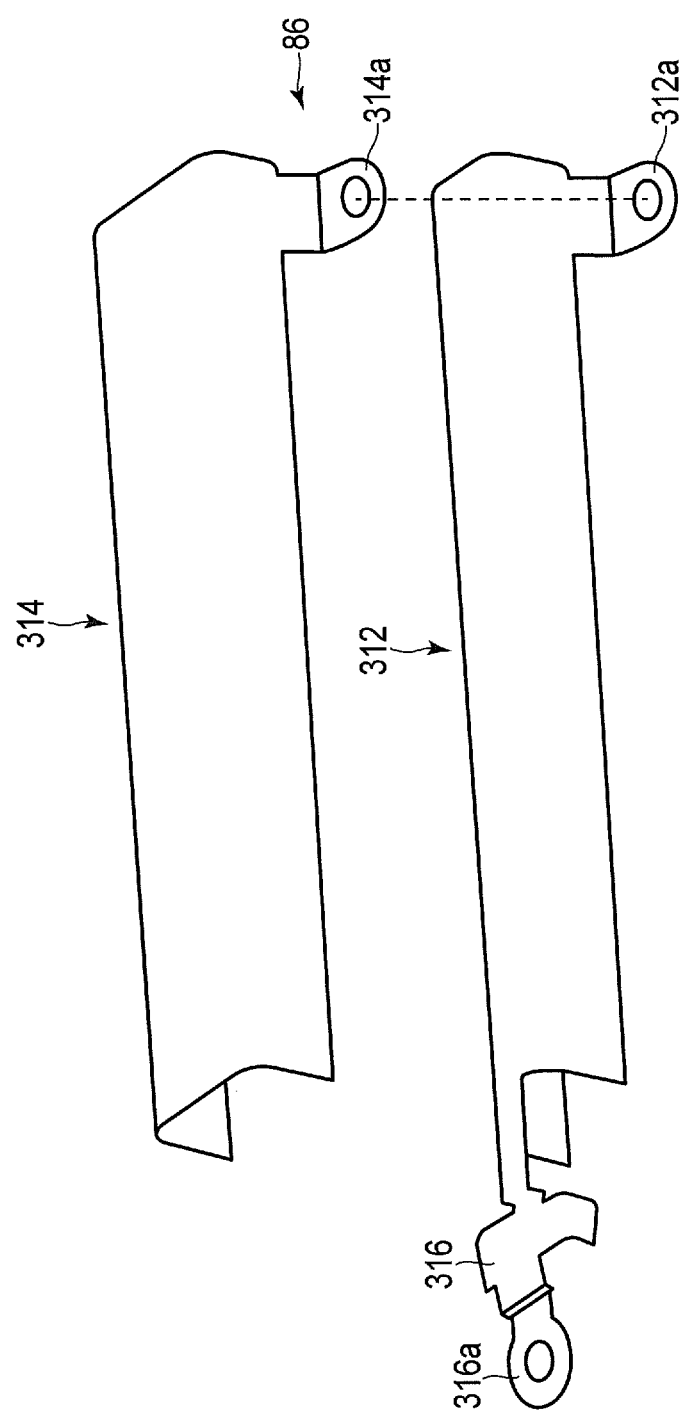

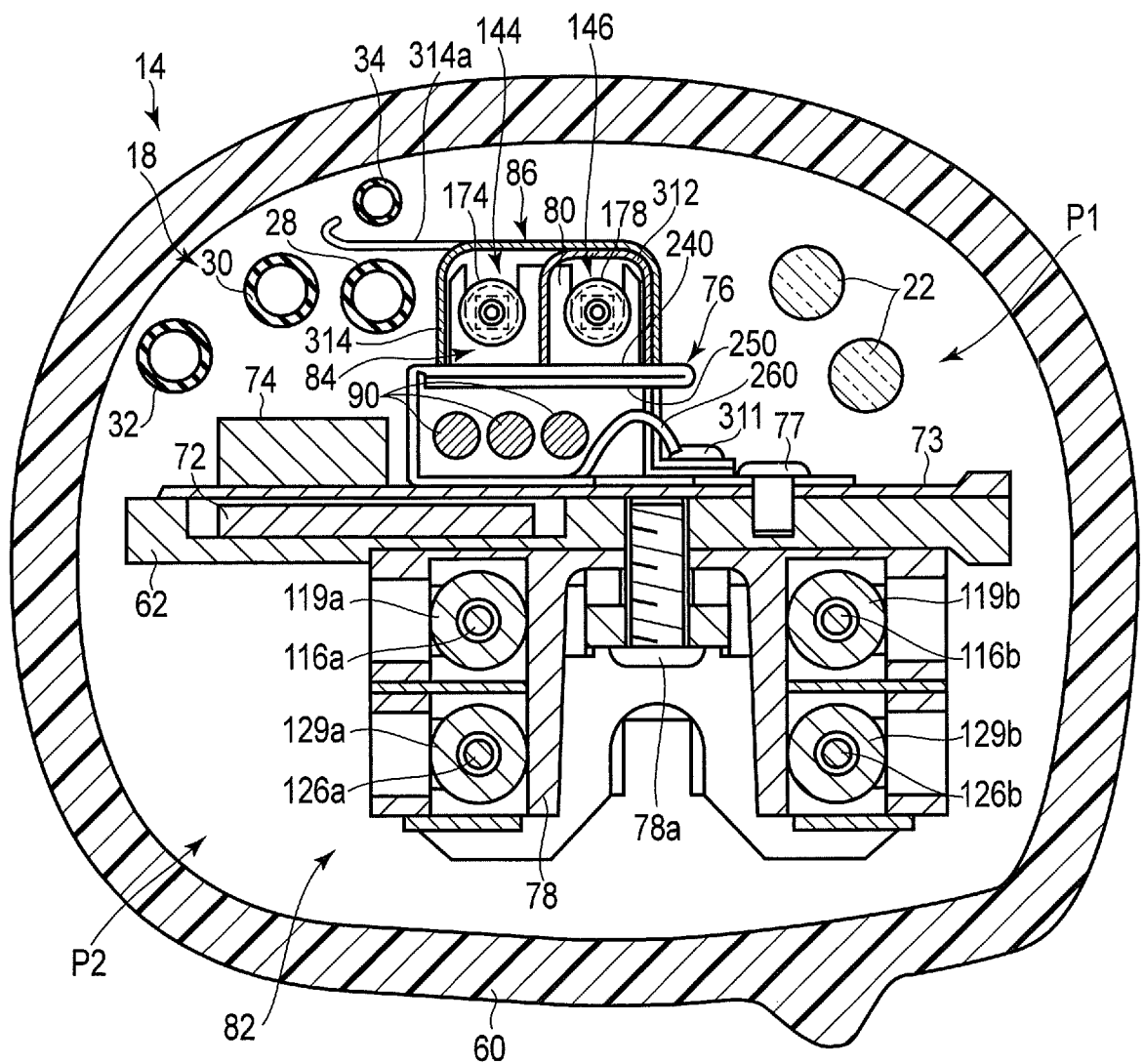
F I G. 13

ENDOSCOPE

CROSS-REFERENCE TO RELATED APPLICATIONS

This application is a Continuation Application of PCT Application No. PCT/JP2017/036505, filed Oct. 6, 2017 and based upon and claiming the benefit of priority from prior Japanese Patent Application No. 2016-208875, filed Oct. 25, 2016, the entire contents of all of which are incorporated herein by reference.

BACKGROUND OF THE INVENTION

1. Field of the Invention

The present invention relates to an endoscope having an insertion section and an operation section.

2. Description of the Related Art

US 2014/200513 A1, for example, discloses an endoscope having one bending section (operation mechanism) in an insertion section. Japanese Patent Application KOKAI Publication No. 2003-093330, for example, discloses an endoscope having two active bending sections (operation mechanisms) in an insertion section.

The endoscope disclosed in US 2014/200513 A1, for example, has a plate-like frame disposed along a longitudinal axis inside an operation section. The frame forms two regions inside the operation section. In one of the regions of the frame, one or a plurality of pairs of pulling sections (wires) for bending the bending section are disposed, and in the other region, an elongated member (built-in object) is disposed.

BRIEF SUMMARY OF THE INVENTION

According to one aspect of the present invention, an endoscope includes an insertion section, an operation section, a first pulling section, a first elongated member, a restricting portion, a sliding surface, and a partition. The insertion section includes a portion to be operated. The operation section is provided on a proximal side of the insertion section. The first pulling section includes: a first wire disposed inside the operation section, and coupled to the operation section, a second wire disposed inside the operation section and the insertion section, and coupled to the portion to be operated of the insertion section, and a connection portion coupling the first wire and the second wire. The first pulling section is configured to move along an axial direction thereof when transmitting an operation performed by the operation section to the portion to be operated of the insertion section. The first elongated member extends inside the operation section and the insertion section. The restricting portion is provided inside the operation section, and configured to restrict a position of the first pulling section. The sliding surface is provided in the restricting portion, and allows the first pulling section to move along the axial direction. The partition covers at least a part of the sliding surface and the first pulling section. The partition is configured to partition the first elongated member and the first pulling section. The partition and the restricting portion are configured to restrict a moving range of the connection portion within a range of the sliding surface.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1B is a schematic view of a distal end of an insertion section observed from a direction of an arrow 1B in FIG. 1A.

FIG. 3B is a schematic diagram showing a part of the second bending drive assembly.

FIG. 10A is a schematic development view of a state in which a part of a broken line of the plate-like member in FIG. 9A is ridge-folded as observed from a direction of an arrow 10A in FIG. 10B.

FIG. 10B is a schematic view of the plate-like member observed from a direction of an arrow 10B in FIG. 10A.

FIG. 12 is a disassembled perspective view showing a state in which a first partitioning member and a second partitioning member of the partition are disassembled.

FIG. 13 is a schematic cross-sectional view showing a state in which a barrier wall for partitioning tubes is formed by cutting and bending a part of the second partitioning member of the partition shown in FIG. 2.

DETAILED DESCRIPTION OF THE INVENTION

Hereinafter, an embodiment for implementing the present invention will be explained with reference to the drawings.

Figure 1A:
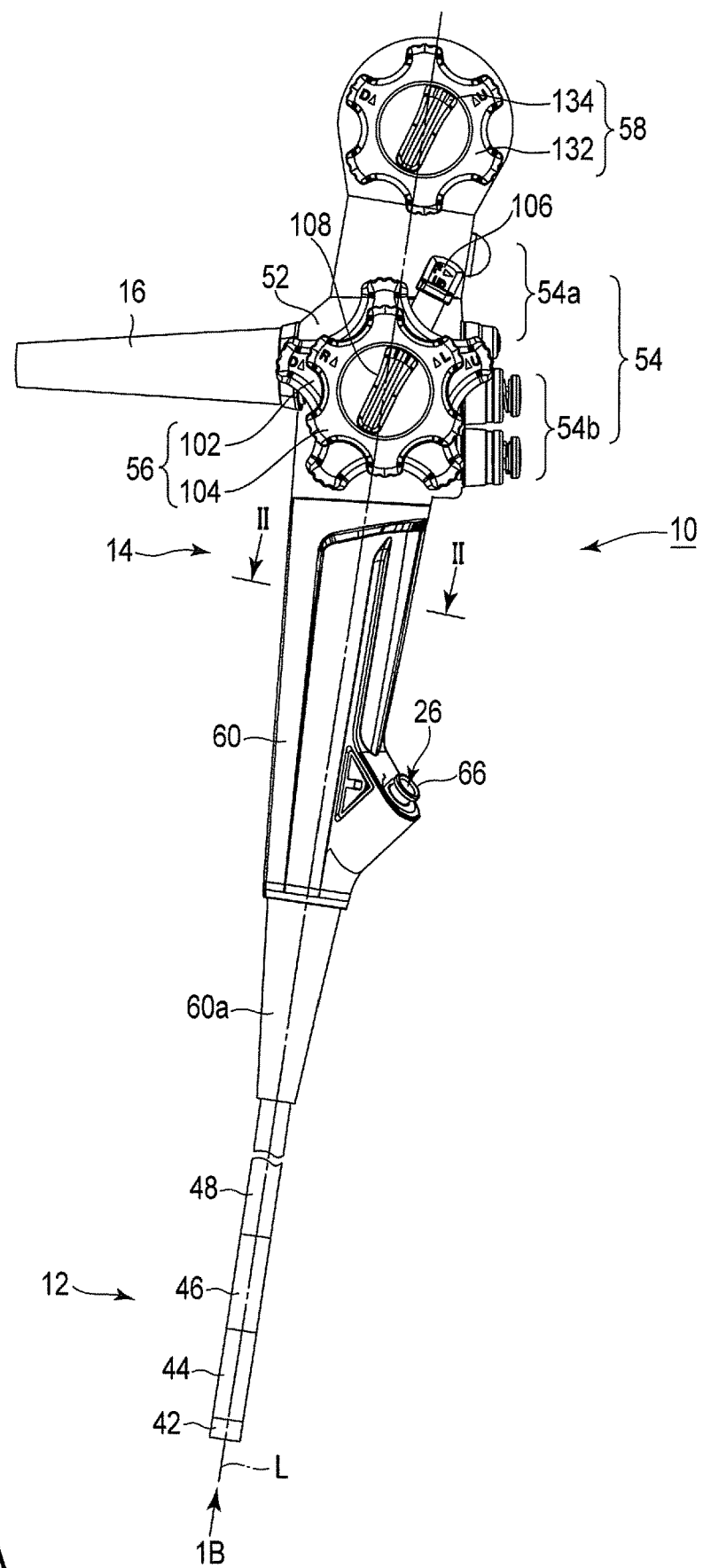
FIG. 1A is a schematic view of an endoscope according to an embodiment.
Figure 2:
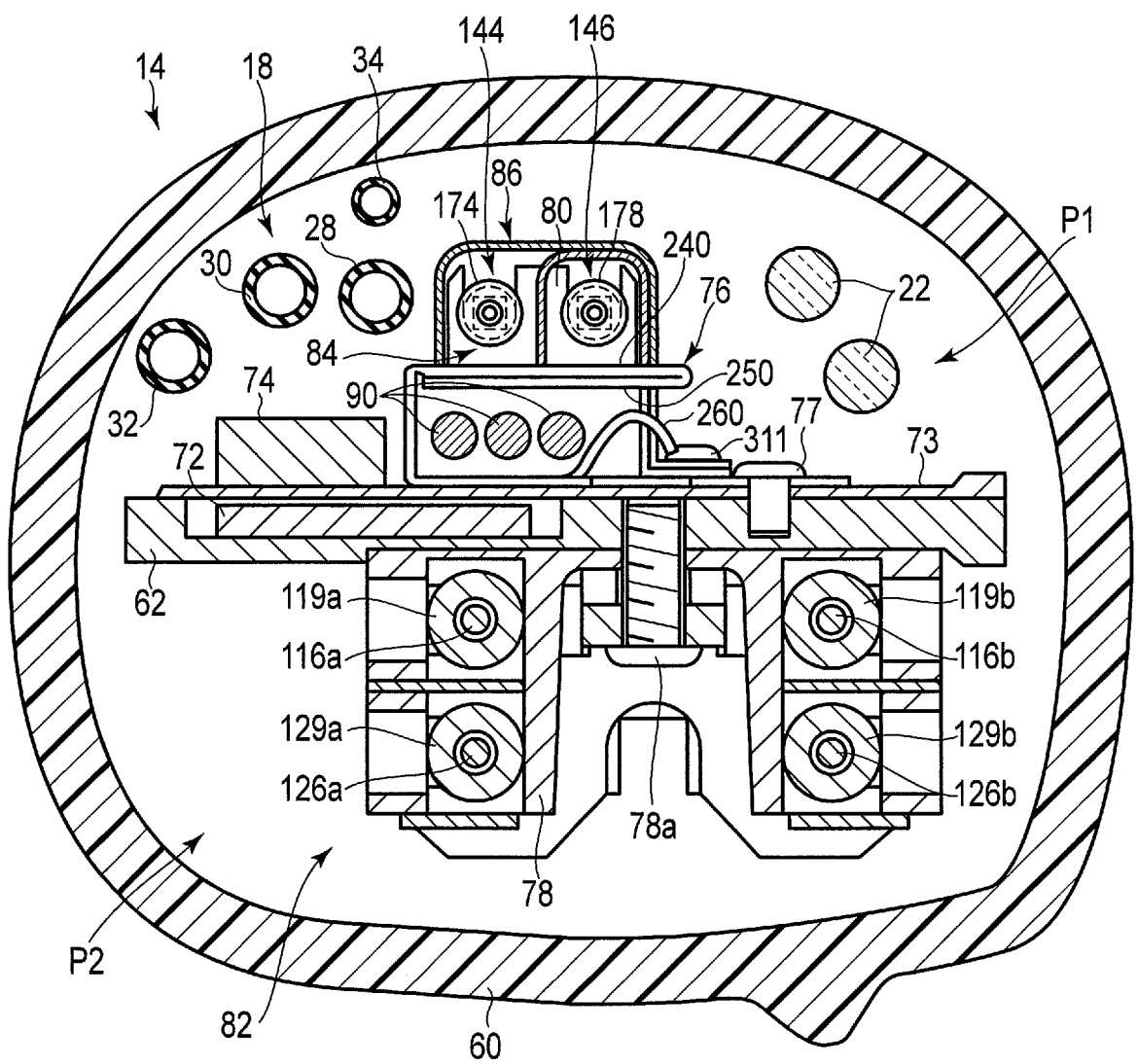
FIG. 2 is a schematic cross-sectional view taken along a line II-II in FIG. 1A.

As shown in FIG. 1A, an endoscope 10 according to the present embodiment includes an insertion section 12 extending along a longitudinal axis L thereof, an operation section 14, and a universal cord 16. Various elongated members (built-in objects) 18 shown in FIG. 1B and FIG. 2 are extended inside the insertion section 12, the operation section 14, and the universal cord 16. Specifically, as the elongated member 18, an illumination optical system 22, an observation optical system 24, a treatment instrument insertion channel 26, a suction tube 28, an air supply tube 30, a water supply tube 32, and an auxiliary water supply tube 34, etc., are disposed inside the insertion section 12, the operation section 14, and the universal cord 16.

For example, a plurality of elongated members 18 may be selected from the illumination optical system 22, the observation optical system 24, the treatment instrument insertion channel 26, the suction tube 28, the air supply tube 30, the water supply tube 32, and the auxiliary water supply tube 34.

The elongated member 18 is not limited to the ones mentioned above. Among the exemplified elongated members 18, for example, the auxiliary water supply tube 34 does not necessarily have to be disposed inside the insertion section 12, the operation section 14, and the universal cord 16. What is disposed inside the operation section 14 is, for example, a light guide or an LED cable in the case of the illumination optical system 22, and is, for example, an imaging cable in the case of the observation optical system 24.

A circuit (not shown) of a substrate 72 described later on is electrically connected to, for example, the observation optical system 24 and a first switch group 54a of the operation section 14 described later on. It is also preferable to have the LED cable electrically connected to the circuit of the substrate 72.

As shown in FIG. 1A, the insertion section 12 includes a distal end configuration portion 42, a first bending section (a portion to be operated) 44, a second bending section (a portion to be operated) 46, and a tubular section 48 from a distal side toward a proximal side thereof in this order. As shown in FIG. 1B, on a distal end surface 42a of the distal end configuration portion 42 are disposed an illumination window at a distal end of the illumination optical system 22, an observation window at a distal end of the observation optical system 24, a distal end opening 26a of the channel 26 and the suction tube 28, a distal-end nozzle 30a to be connected to the air supply tube 30 (see FIG. 2) and the water supply tube 32 (see FIG. 2), and a distal end opening 31 of the auxiliary water supply tube 34.

It is preferable to respectively form the first bending section 44 and the second bending section 46 bendable in a U (Up) direction, a D (Down) direction, an R (Right) direction and an L (Left) direction. The bending angles of the first bending section 44 and the second bending section 46 are respectively set to an appropriate angle from 0° (a state in which the first bending section 44 and the second bending section 46 are straight along the longitudinal axis L).

Although explanations will be omitted on well-known matters, the first bending section 44 includes, for example, in the order from the inside to the outside, a bending tube formed of a plurality of bending pieces (nodal rings) coupled along the longitudinal axis L of the insertion section 12, a braid (braided tube), and an outer tube. Furthermore, the braid between the bending tube and the outer tube does not have to be provided.

It is also preferable to form the second bending section 46 in the same structure as the first bending section 44. The lengths of the first bending section 44 and the second bending section 46 along the longitudinal axis L may be the same or different, and can be set as appropriate.

It is preferable to form the tubular section 48 in a flexible state, in which it has flexibility, and is bendable in accordance with a load of an external force. The tubular section 48 may also be formed in a rigid state, in which its shape is maintained by a rigid tube even when receiving a load of an external force.

The operation section 14 is provided on a proximal side of the insertion section 12. The operation section 14 is configured to operate the insertion section 12 as appropriate. The operation section 14 includes a main body 52, a plurality of switch groups 54, a first operation knob (a first operation section of the first bending section) 56, a second operation knob (a second operation section of the second bending section) 58, and a grip 60. The first operation knob 56 is disposed on the main body 52. The grip 60 is coupled to the main body 52. The universal cord 16 is extended from the main body 52.

A user can grasp the main body 52 and the grip 60 with the left hand in a state where the universal cord 16 is placed near the base of the thumb and the forefinger of the left hand. Since the switch groups 54 are respectively publicly-known, detailed explanations thereof will not be made; however, they include the first switch group 54a operated by electrical connection by pressing, etc., and a second switch group 54b mechanically operated by pressing, etc.

The first switch group 54a is, for example, a release switch and an illumination light changeover switch for switching between white light and narrow-band imaging (NBI), and is used, for example, for switching electric signals. The second switch group 54b is, for example, a suction switch and an air/water supply switch, and is used, for example, for mechanical switching.

Figure 3A:
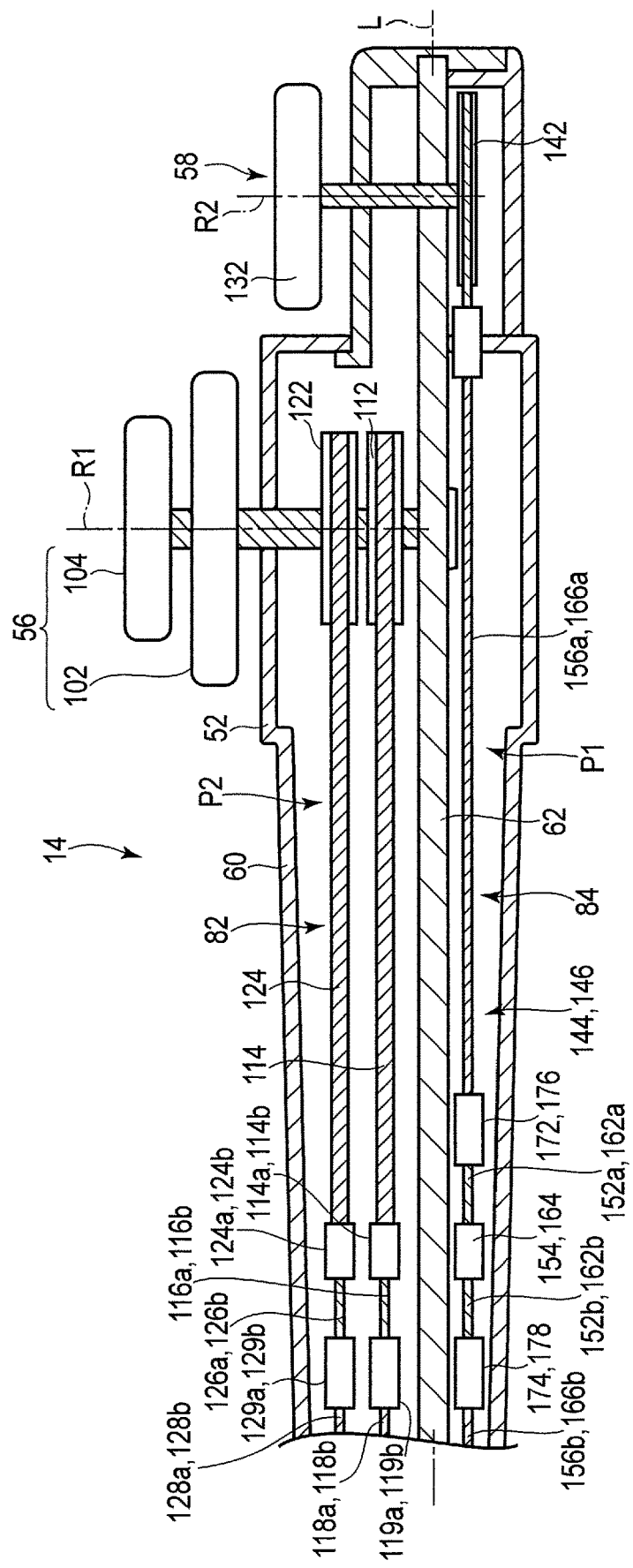
FIG. 3A is a schematic diagram showing a part of a first bending drive assembly driven by operating a first operation knob, and a part of a second bending drive assembly driven by operating a second operation knob of the endoscope according to the embodiment.
Figure 5:
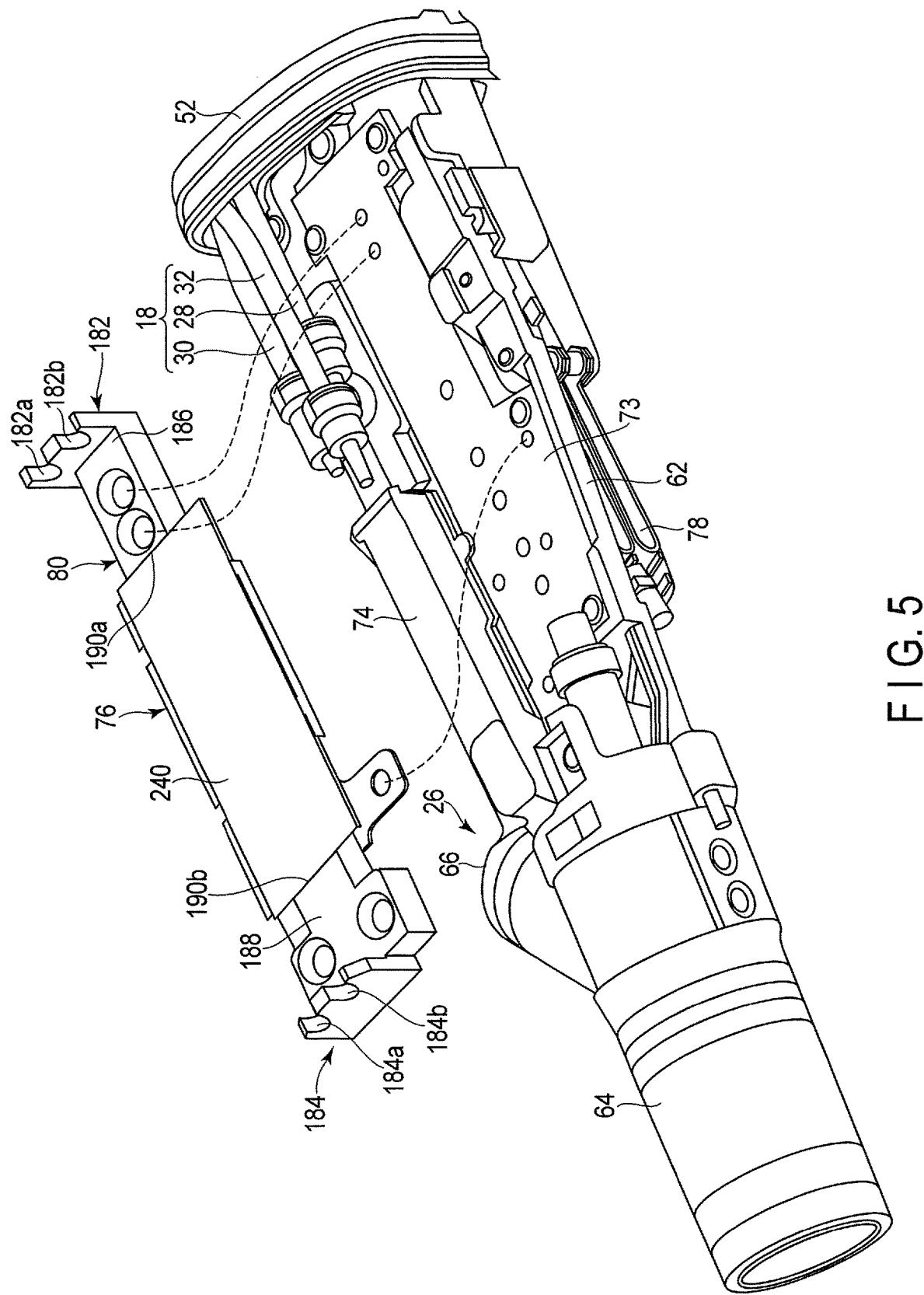
FIG. 5 is a schematic perspective view showing a state in which a base plate is disposed in a first section partitioned by a frame inside an operation section of the endoscope according to the embodiment, and a state in which a restricting portion on which a cable holder is disposed is attachable to the frame via the base plate.
Figure 6:
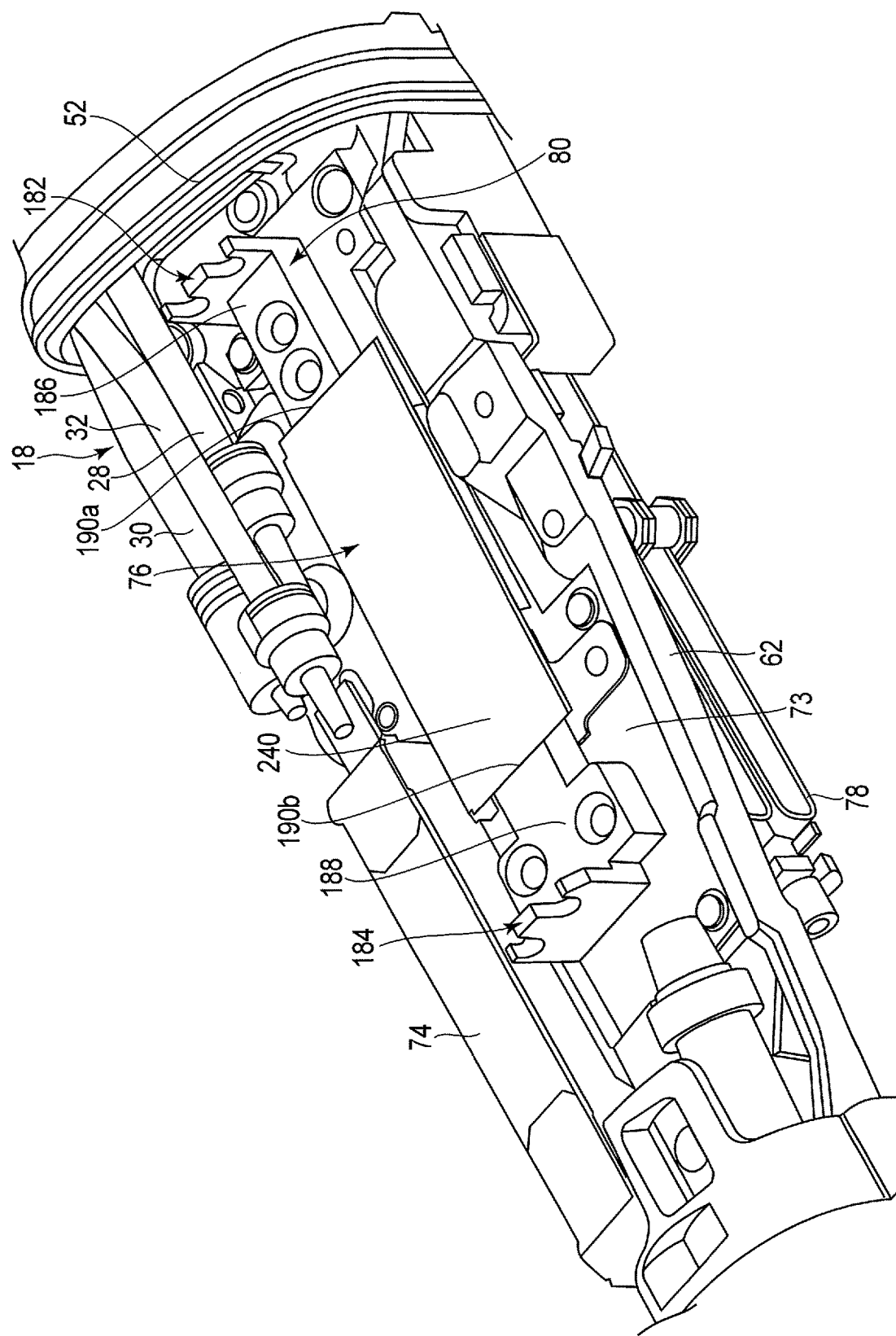
FIG. 6 is a schematic perspective view showing a state in which a restricting portion on which a cable holder is disposed is attached to a frame via a base plate disposed in a first section partitioned by a frame inside an operation section of the endoscope according to the embodiment.

As shown in FIG. 3A, the operation section 14 includes therein a frame 62 extending along the longitudinal axis L. As shown in FIG. 5, the frame 62 includes a pipe sleeve 64 to which the proximal end of the tubular section 48 of the insertion section 12 is connected, and a proximal end opening 66 communicating with the treatment instrument insertion channel 26. The proximal end of the tubular section 48 of the insertion section 12 shown in FIG. 1A is coupled to the pipe sleeve 64 of the frame 62 inside a bending stopper 60a.

The frame 62 is formed into a plate-like shape extending along the longitudinal axis L. As shown in FIG. 2 and FIG. 3A, the frame 62 cooperates with the inner peripheral surface of the main body 52 and the grip 60 of the operation section 14, and separates the inside of the operation section 14 into a first section P1 and a second section P2. Therefore, the first section P1 and the second section P2 are disposed on opposite sides of the frame 62 each other.

A substrate 72, a cable relay substrate 74, a conductive cable holder (built-in object protecting body) 76 formed into a box shape, a first restricting portion 78, a second restricting portion 80, a first bending drive assembly (drive mechanism) 82, a second bending drive assembly (drive mechanism) 84, and a partition (tunnel-shaped cover) 86 are disposed on the frame 62. That is, the frame 62, the substrate 72, the cable relay substrate 74, the cable holder (built-in object protecting body) 76, the first restricting portion 78, the second restricting portion 80, the first bending drive assembly 82, the second bending drive assembly 84, and the partition 86 are provided inside the operation section 14.

Each of a part of the substrate 72, the cable relay substrate 74, the cable holder 76, the second restricting portion 80, and the second bending drive assembly 84 is fixed in the first section P1 by the frame 62. Here, the base plate 73 fixed to the frame 62 prevents the substrate 72 from abutting the elongated member (built-in object) 18. It is preferable to have the base plate 73 formed into a substantially flat plate shape. The cable relay substrate 74, the second restricting portion 80, and the cable holder 76 may be fixed to the frame 62 interposing the substrate 72 therebetween.

Each of a part of the first restricting portion 78 and the first bending drive assembly 82 is fixed in the second section P2 by the frame 62. The first restricting portion 78 is fixed to the frame 62 by a screw 78a.

The first restricting portion 78 is configured to restrict positions of coil sheaths 118a, 118b, 128a, and 128b, which will be described later, of the first bending drive assembly 82. In the first bending drive assembly 82, a first sprocket 112 and a second sprocket 122, which will be described later, are supported by the frame 62.

The second restricting portion 80 is configured to restrict positions of a pulling section (hereinafter referred to as a first pulling section) 144 and another pulling section (hereinafter referred to as a second pulling section) 146, described later, of the second bending drive assembly 84. In the second bending drive assembly 84, a pulley 142, which will be described later, is supported by the frame 62. The substrate 72 is electrically connected to a signal line of the illumination optical system 22 and/or the observation optical system 24, or a signal line of the switch group 54, etc. The cable holder 76 holds the cable 90 serving as an appropriate signal line, and surrounds it with a conductive member to prevent electromagnetic influence from occurring on a signal in the signal line.

FIG. 3A shows a schematic diagram of the first bending drive assembly 82 and the second bending drive assembly 84.

The first operation knob 56 is used to bend the first bending section 44 in an appropriate direction. The first operation knob 56 includes a first rotating member 102 operated when the first bending section 44 is bent in the U direction or the D direction, and a second rotating member 104 disposed on the same axis (R1) as the first rotating member 102 and operated when the first bending section 44 is bent in the R direction or the L direction.

A brake lever 106 (see FIG. 1A) for controlling the rotation of the first rotating member 102 is disposed between the first rotating member 102 and the main body 52. By appropriately operating the brake lever 106, the rotation of the first rotating member 102 can be controlled. Since a brake mechanism using the brake lever 106 is public knowledge, the explanation thereof will be omitted.

A brake handle 108 (see FIG. 1A) that controls the rotation of the second rotating member 104 is disposed on the second rotating member 104. By operating the brake handle 108, the rotation of the second rotating member 104 can be controlled. Since the brake mechanism using the brake handle 108 is public knowledge, the explanation thereof will be omitted.

The first bending drive assembly 82 is disposed between the first operation knob 56 and the first bending section 44. The first bending drive assembly 82 includes the first sprocket 112 rotating in accordance with the rotation of the first rotating member 102, a first chain 114 engaged with the first sprocket 112, a U-wire 116a and a D-wire 116b coupled to end portions 114a and 114b of the first chain 114, and the second sprocket 122 that rotates in accordance with the rotation of the second rotating member 104, a second chain 124 engaged with the second sprocket 122, and an R-wire 126a and an L-wire 126b coupled to end portions 124a and 124b of the second chain 124.

The U-wire 116a and the D-wire 116b are inserted through the coil sheaths 118a and 118b. The R-wire 126a and the L-wire 126b are inserted through the coil sheaths 128a and 128b. End portions 119a, 119b, 129a, and 129b of the coil sheaths 118a, 118b, 128a, and 128b are supported by the first restricting portion 78 of the frame 62.

Although not shown, it is preferable to have the distal ends of the coil sheaths 118a, 118b, 128a, and 128b fixed to a bending piece at the most proximal end of a plurality of bending pieces of the first bending section 44. Although not shown, it is preferable to have the distal ends of the U-wire 116a, the D-wire 116b, the R-wire 126a, and the L-wire 126b fixed to a bending piece of the most distal end of a plurality of bending pieces of the first bending section 44.

In conjunction with the rotation of the first rotating member 102, the first sprocket 112, the first chain 114, the U-wire 116a, and the D-wire 116b move in the axial direction thereof. In this manner, the U-wire 116a and the D-wire 116b transmit a driving force of the operation section 14 to the first bending section 44. That is, the U-wire 116a and the D-wire 116b are moving members that move along the axial direction thereof by an operation of the operation section 14, and that are configured to bend the first bending section of the insertion section 12 in the U direction or the D direction.

In conjunction with the rotation of the second rotating member 104, the second sprocket 122, the second chain 124, the R-wire 126a, and the L-wire 126b move in the axial direction thereof. In this manner, the R-wire 126a and the L-wire 126b transmit a driving force of the operation section 14 to the first bending section 44. That is, the R-wire 126a and the L-wire 126b are moving members that move along the axial direction thereof by an operation of the operation section 14, and that are configured to bend the first bending section of the insertion section 12 in the R direction or the L direction.

The second operation knob 58 is used to bend the second bending section 46 in an appropriate direction (for example, the U direction or the D direction). The second operation knob 58 is operated when bending the second bending section 46 in the U direction or the D direction. The second operation knob 58 includes a rotating member 132 and a brake handle 134 (see FIG. 1A).

The rotating member 132 of the second operation knob 58 is rotatable about the axis of an axis R2 that is parallel to an axis R1 of the first rotating member 102 and the second rotating member 104 of the first operation knob 56. The brake handle 134 for controlling the rotation of the second operation knob 58 is disposed on the rotating member 132 of the second operation knob 58. Since the brake handle 134 has a structure similar to that of the brake handle 108 of the second rotating member 104 of the above-described first operation knob 56, and is of public knowledge, explanations thereof will be omitted.

The second bending drive assembly 84 is disposed between the second operation knob 58 and the second bending section 46. The second bending drive assembly 84 includes a pulley 142 that rotates in accordance with the rotation of the second operation knob 58, a pulling section coupled to the pulley 142, that is, a first pulling section (U-direction pulling member) 144, and a second pulling section (D-direction pulling member) 146, which is a different pulling section from the first pulling section 144 coupled to the pulley 142. The first pulling section 144 and the second pulling section 146 are disposed inside the operation section 14 and the insertion section 12. The first pulling section 144 and the second pulling section 146 move along the axial direction thereof when transmitting the operation of the operation section 14 to the second bending section 46 of the insertion section 12. The first pulling section 144 and the second pulling section 146 are juxtaposed to each other, and selectively exercise a pulling force in accordance with the rotation direction of the pulley 142.

If the second bending section 46 needs to be bent only in the U direction, the second pulling section 146 is unnecessary. If the second bending section 46 needs to be bent only in the D direction, the first pulling section 144 is unnecessary. That is, the second bending drive assembly 84 may be configured to include only one of the first pulling section 144 and the second pulling section 146.

The first pulling section 144 includes a first U-wire (first wire) 152a, a second U-wire (second wire) 152b, a first connection portion 154, a first U-coil pipe (first coil pipe) 156a, and a second U-coil pipe (second coil pipe) 156b. The proximal end of the first U-wire 152a is coupled to the pulley 142. The distal end of the second U-wire 152b is preferable to be fixed to the most distal end bending piece of the plurality of bending pieces of the second bending section 46. The first U-wire 152a is inserted through the first U-coil pipe 156a. The second U-wire 152b is inserted through the second U-coil pipe 156b.

Figure 4:
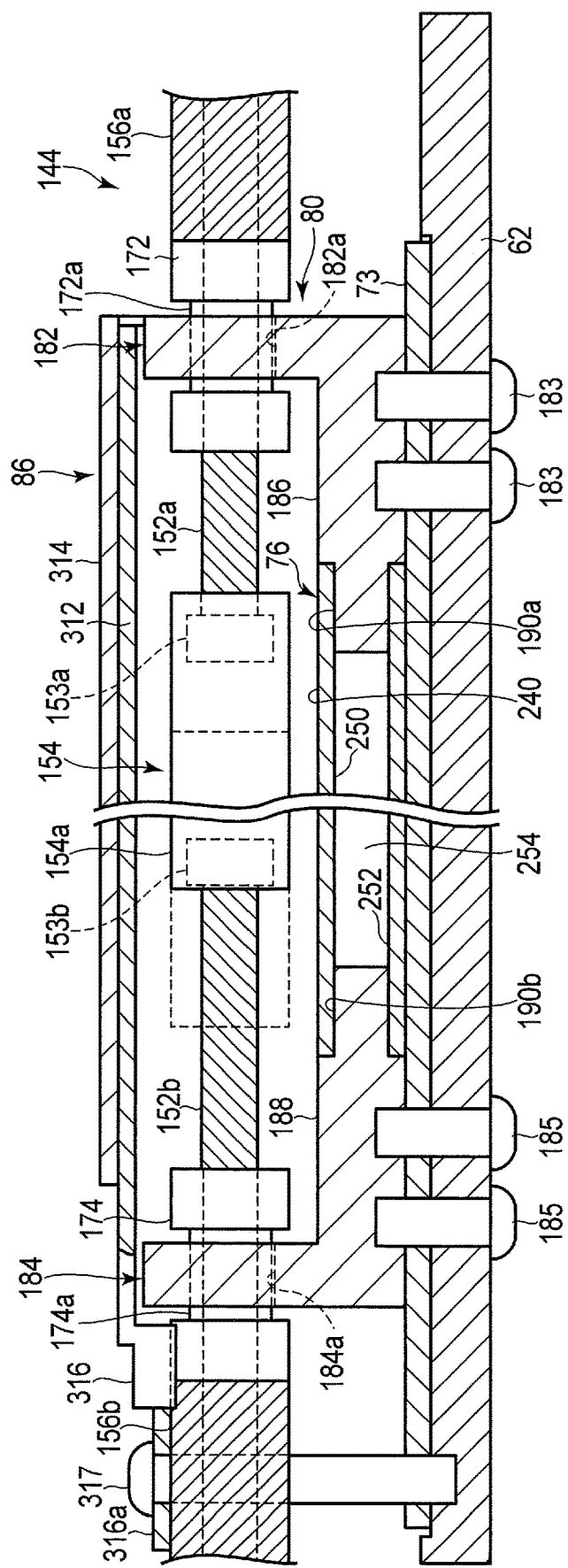
FIG. 4 is a schematic partial cross-sectional view taken along a line IV-IV in FIG. 8, showing a state of a first section with respect to a frame inside an operation section of the endoscope according to the embodiment.

As shown in FIG. 3B and FIG. 4, a pipe-shaped pipe end (pipe sleeve) 172 is fixed to the distal end of the first U-coil pipe 156a, and a pipe-shaped pipe end 174 is fixed to the proximal end of the second U-coil pipe 156b. Annular grooves 172a and 174a are formed respectively on the outer peripheral surfaces of the pipe ends 172 and 174.

The position of the pipe end 172 at the distal end of the first U-coil pipe 156a is restricted by the second restricting portion 80. The position of the pipe end 174 at the proximal end of the second U-coil pipe 156b is restricted by the second restricting portion 80. The distal end 172 of the first U-coil pipe 156a and the proximal end 174 of the second U-coil pipe 156b are separated along the longitudinal axis L.

The first connection portion 154 that couples the distal end of the first U-wire 152a to the proximal end of the second U-wire 152b is disposed between the distal end 172 of the first U-coil pipe 156a and the proximal end 174 of the second U-coil pipe 156b. The wires 152a and 152b are configured to operate the second bending section 46. The first U-wire 152a of a side of the operation section 14 connects to the second U-wire 152b of a side of the insertion section 12 by a cylindrical body 154a of the first connection portion 154 that reciprocates on a traveling surface of the pulling section 144.

The first connection portion 154 is used for adjusting the length and tension of the first U-wire 152a and the second U-wire 152b. Depending on the state of the first connection portion 154, the first U-wire 152a and the second U-wire 152b may be deflected. In such case, the first connection portion 154 may come in contact with the inner peripheral surface of a sliding surface 240 and/or a first partitioning member (built-in object protecting member) 312 described later. The sliding surface 240 allows the first pulling section 144 to move along the axial direction.

As shown in FIG. 3B and FIG. 4, a distal end 153a of the first U-wire 152a is disposed inside the cylindrical body 154a of the first connection portion 154. A proximal end 153b of the second U-wire 152b is disposed inside the cylindrical body 154a of the first connection portion 154. The distal end 153a of the first U-wire 152a and the proximal end 153b of the second U-wire 152b face each other along the longitudinal axis L inside the cylindrical body 154a of the first connection portion 154. The distal end 153a of the first U-wire 152a and the proximal end 153b of the second U-wire 152b are able to move along the longitudinal axis L inside the tubular body 154a of the first connection portion 154, and can become proximate (abut) and separated.

Therefore, the first connection portion 154 supports the end portion (distal end) 153a of the first U-wire 152a and the end portion (proximal end) 153b of the second U-wire 152a movable along the longitudinal axis L of the tubular body 154a. Therefore, the first connection portion 154 can move along the longitudinal axis L in conjunction with the movement of the first U-wire 152a and/or the second U-wire 152b.

As shown in FIG. 3A, the second pulling section 146 includes a first D-wire 162a, a second D-wire 162b, a second connection portion 164, a first D-coil pipe 166a, and a second D-coil pipe 166b. The second pulling section 146 is preferable to have a structure similar to that of the first pulling section 144. The proximal end of the first D-wire 162a is coupled to the pulley 142. The distal end of the first D-wire 162a is coupled to the second connection portion 164. The proximal end of the second D-wire 162b is coupled to the second connection portion 164. The distal end of the first D-wire 162a and the proximal end of the second D-wire 162b face each other along the longitudinal axis L at the second connection portion 164.

Figure 7:
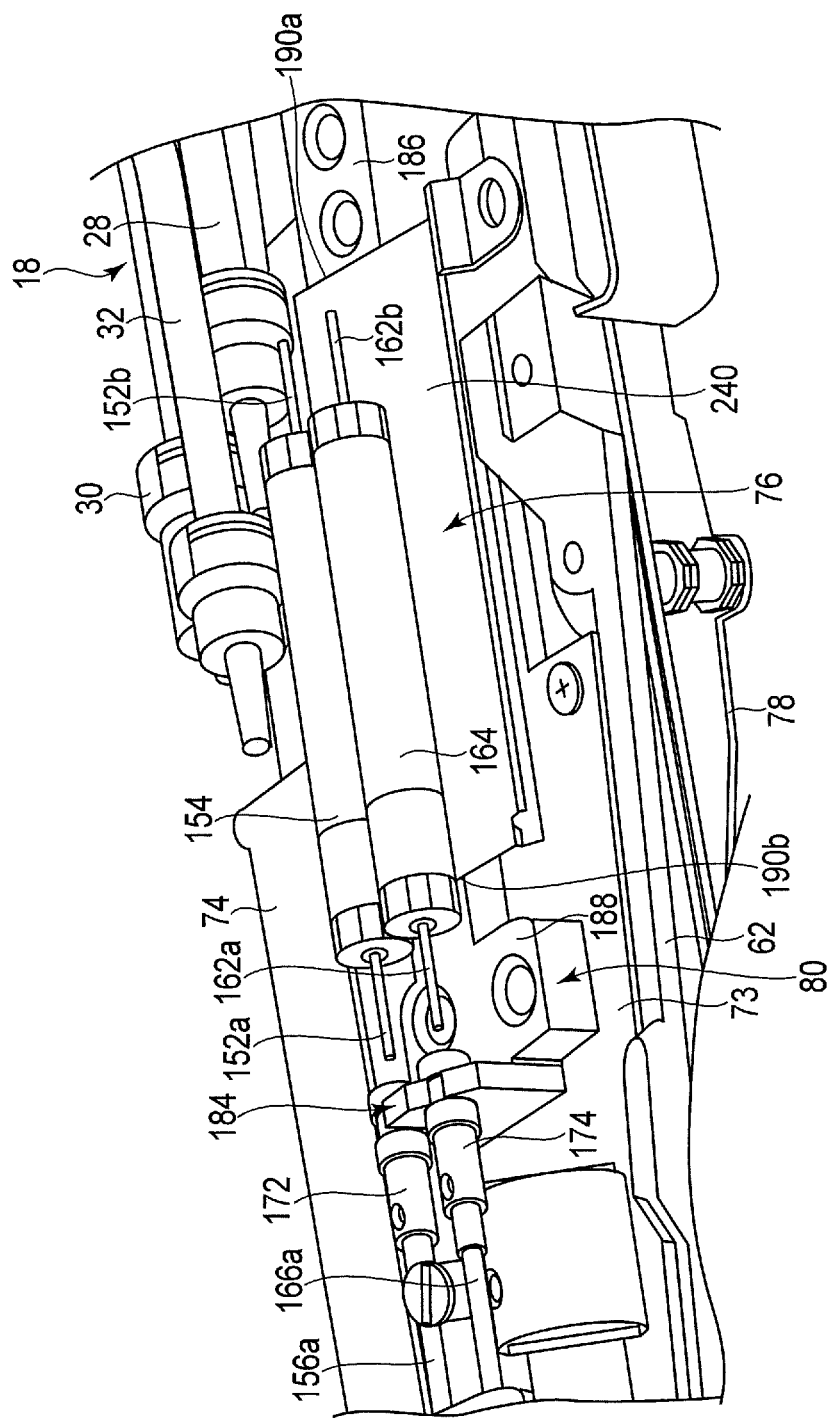
FIG. 7 is a schematic perspective view showing a state in which a first connection portion of a first pulling section and a second connection portion of a second pulling section are disposed on a sliding surface of the cable holder in FIG. 6.

Although not shown, it is preferable that the second connection portion 164 is formed in the same manner as the first connection portion 154 (see FIG. 7). It is preferable that the distal end of the second D-wire 162b is fixed to the most distal bending piece of the plurality of bending pieces of the second bending section 46.

The first D-wire 162a is inserted through the first D-coil pipe 166a. The second D-wire 162b is inserted through the second D-coil pipe 166b. A pipe-shaped pipe end (pipe sleeve) 176 is fixed to the distal end of the first D-coil pipe 166a. A pipe-shaped pipe end (pipe sleeve) 178 is fixed to the proximal end of the second D-coil pipe 166b. An annular groove is respectively formed on the outer peripheral surfaces of the pipe ends 176 and 178 in a manner similar to the outer peripheral surfaces of the pipe ends 172 and 174 (see FIG. 7). Therefore, the positions of the distal end of the first D-coil pipe 166a and the proximal end of the second D-coil pipe 166b are respectively restricted by a second engaging portion 184 of the second restricting portion 80 described later on.

The distal end of the first D-coil pipe 166a and the proximal end of the second D-coil pipe 166b are separated along the longitudinal axis L. The second connection portion 164 for coupling the first D-wire 162a to the second D-wire 162b is disposed between the distal end of the first D-coil pipe 166a and the proximal end of the second D-coil pipe 166b. The second connection portion 164 supports the end portion (distal end) of the first D-wire 162a and the end portion (proximal end) of the second D-wire 162b movably along the longitudinal axis L of the cylindrical body. Therefore, the second connection portion 164 is movable along the longitudinal axis L in synchronization with the movement of the first D-wire 162a and/or the second D-wire 162b.

The second connection portion 164 is used for adjusting the length and tension of the first D-wire 162a and the second D-wire 162b. Depending on the state of the second connection portion 164, the first D-wire 162a and the second D-wire 162b may be deflected. In such case, the second connection portion 164 may come in contact with the later-described sliding surface 240, and/or the outer peripheral surface of the first partitioning member 312, and/or the inner peripheral surface of a second partitioning member (built-in object protecting member) 314. The sliding surface 240 allows the second pulling section 146 to move along the axial direction.

As described above, the pipe ends 172, 174, 176, and 178 at the end portions of the coil pipes 156a, 156b, 166a, and 166b are supported and positioned by the second engaging portion 184, described later, of the second restricting portion 80 that restricts the positions of the first pulling section 144 and the second pulling section 146. Here, although an example of the second engaging portion 184 of the second restricting portion 80 being fixed to the frame 62 by screws 183 and 185 is explained, the second engaging portion 184 may also be integrated with the frame 62.

FIG. 5 to FIG. 8 show an assembly procedure for disposing with respect to the frame 62 and the base plate 73 the second engaging portion 184 of the second restricting portion 80 on which the cable holder 76 is disposed, the first connection portion 154, the second connection portion 164, and the partition 86 in this order. FIG. 12 is an exploded perspective view of the partition 86 shown in FIG. 8. FIG. 4 is a partial cross-sectional view of an appropriate position in FIG. 8 in the first section P1.

As shown in FIG. 4 to FIG. 8, the second restricting portion 80 includes a first engaging portion (proximal side engaging portion) 182 and the second engaging portion (distal side engaging portion) 184. The first engaging portion 182 and the second engaging portion 184 are separated from each other. The first engaging portion 182 and the second engaging portion 184 are fixed to the frame 62 via the base plate 73. Each of the first engaging portion 182 and the second engaging portion 184 is fixed to the frame 62 by, for example, a plurality of screws 183 and 185. Therefore, the first engaging portion 182 and the second engaging portion 184 are respectively prevented from rotating with respect to the frame 62.

In the present embodiment, an example of the cable holder 76 being fixed to the frame 62 in a state where it is wound around the first engaging portion 182 and the second engaging portion 184 of the second restricting portion 80 will be explained. It is also preferable to merely place the cable holder 76 in a concave portion formed between the first engaging portion 182 and the second engaging portion 184 of the second restricting portion 80.

The base plate 73 is formed in a manner that a direction along the longitudinal axis L is made longer than a width direction that is orthogonal to the longitudinal axis L. The first engaging portion 182 is fixed in the vicinity of one end (proximal end) of the base plate 73, and the second engaging portion 184 is fixed in the vicinity of the other end (distal end) of the base plate 73 along the longitudinal axis L.

A first extending portion (flat portion) 186 provided along the extending direction of the first pulling section 144 and the second pulling section 146 is disposed on the first engaging portion 182. The first extending portion 186 extends toward the second engaging portion 184. The first extending portion 186 is formed into a smooth flat surface. It is preferable to form the first engaging portion 182 integrally with the first extending portion 186. That is, the first engaging portion (projecting portion) 182 is disposed on the first extending portion 186 in a manner projecting from the first extending portion 186 towards a direction intersecting the direction in which the first pulling section 144 extends. It is preferable that the first extending portion 186 is parallel to the base plate 73.

A second extending portion (flat portion) 188 provided along a direction in which the first pulling section 144 and the second pulling section 146 extend is disposed on the second engaging portion 184. The second extending portion 188 extends toward the first engaging portion 182. The second extending portion 188 is formed into a smooth flat surface. It is preferable to form the second engaging portion 184 integrally with the second extending portion 188. That is, the second engaging portion (projecting portion) 184 is disposed on the second extending portion 188 in a manner projecting from the second extending portion 188 towards a direction intersecting the direction in which the second pulling section 146 extends.

It is preferable that the second extending portion 188 is parallel to the base plate 73. It is preferable that the first extending portion 186 and the second extending portion 188 are flush with each other.

Concave portions 190a and 190b on which the cable holder 76 is to be disposed are formed between an end portion of the first extending portion 186 that is close to the second engaging portion 184 and an end portion of the second extending portion 188 that is close to the first engaging portion 182.

The cable holder 76 is disposed between the concave portions 190a and 190b. Therefore, the cable holder 76 is disposed on the restricting portion 80. The later-described sliding surface (traveling surface on which the connection portions 154 and 164 of the pulling sections 144 and 146 reciprocate) 240 of the cable holder 76 is disposed between the first extending portion 186 and the second extending portion 188. That is, the sliding surface 240 that allows the pulling sections 144 and 146 to move along the axial direction is provided on the restricting portion 80.

The sliding surface 240 of the cable holder 76, the first extending portion 186, and the second extending portion 188 are flush with each other. Therefore, the sliding surface 240 is continuously formed with respect to the extending portions 186 and 188.

Depending on the position of the sliding surface 240 with respect to the restricting portion 80, the first connection portion 154 and the second connection portion 164 may slide not only on the sliding surface 240 but also between the sliding surface 240 and the first extending portion 186. Alternatively, the first connection portion 154 and the second connection portion 164 may slide between the sliding surface 240 and the second extending portion 188.

It is preferable that the gap between the sliding surface 240 and the first extending portion 186 and the gap between the sliding surface 240 and the second extending portion 188 are respectively formed to such an extent that they can be regarded as being flush with the first connection portion 154 and the second connection portion 164. In this case, the first connection portion 154 and the second connection portion 164 can be suppressed from being caught between the sliding surface 240 and the first extending portion 186, or between the sliding surface 240 and the second extending portion 188.

The first engaging portion 182 and the second engaging portion 184 project, for example, in a direction orthogonal to the longitudinal axis L. The first engaging portion 182 includes, for example, a first U-concave portion 182a and a first D-concave portion 182b, each substantially being U-shaped. The annular groove 172a of the pipe end 172 at the end portion of the first U-coil pipe 156a is engaged with the first U-concave portion 182a of the first engaging portion 182. Therefore, the movement of the end portion of the first U-coil pipe 156a along the longitudinal axis L is restricted with respect to the frame 62 by the restricting portion 80.

Therefore, the first U-concave portion 182a of the first engaging portion 182 engages with the end portion of the first U-coil pipe 156a of the first pulling section 144 to restrict its position. Similarly, the first D-concave portion 182b of the first engaging portion 182 engages with the end portion of the first D-coil pipe 166a of the second pulling section 146 to restrict its position.

Similarly, the second engaging portion 184 includes, for example, a second U-concave portion 184a and a second D-concave portion 184b, each substantially being U-shaped. The second U-concave portion 184a of the second engaging portion 184 engages with the end portion of the second U-coil pipe 156b of the first pulling section 144 to restrict its position. The second D-concave portion 184b of the second engaging portion 184 engages with the end portion of the second D-coil pipe 166b of the second pulling section 146 to restrict its position.

On the frame 62, for example, the cable holder 76 for holding the cable 90 connected to the substrate 72 in a predetermined state is fixed by screws 77 via the base plate 73.

The cable 90 is electrically connected to, for example, a cable (not shown) extended from an imaging unit such as a CMOS or CCD (not shown) of the observation optical system 24. Therefore, the cable 90 is formed as a part of the elongated member 18 (one of the various elongated members 18). The cable holder 76 is formed by bending a thin plate-shaped member 210, and is used as an electromagnetic shield (metal shield) for suppressing electromagnetic influence on the cable 90 inside the cable holder 76. The cable 90 may also be extend directly from the imaging unit.

The conductive plate-like member 210 forming the cable holder 76 is formed by a flat plate shown in the development view in FIG. 9A to FIG. 11B.

Figure 9A:
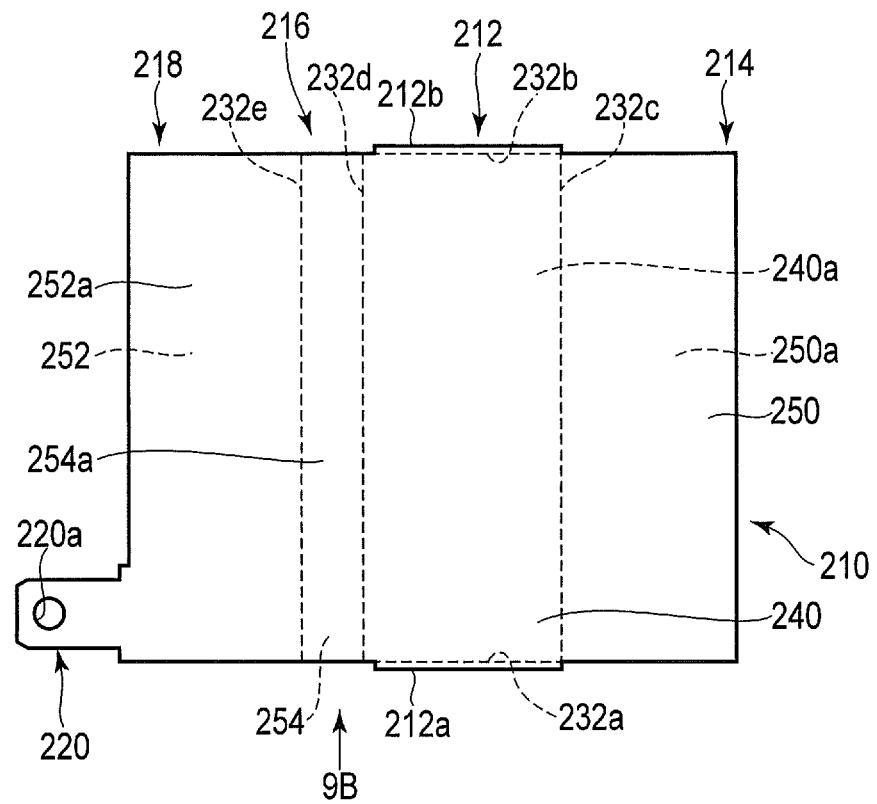
FIG. 9A is a schematic development view of a state in which a plate-like member configuring the cable holder is developed as observed from a direction of an arrow 9A in FIG. 9B.
Figure 9B:
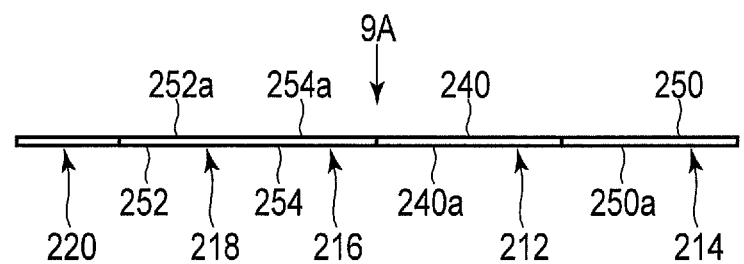
FIG. 9B is a schematic view of the plate-like member observed from a direction of an arrow 9B in FIG. 9A.

The plate-like member 210 shown in FIG. 9A and FIG. 9B is formed into a substantially rectangular shape. The plate-shaped member 210 has a first region 212 in which a pair of tabs 212a and 212b is formed at a position including an end portion (end surface), a second region 214 adjacent to the first region 212, a third region 216 adjacent to the first region 212, and a fourth region 218 adjacent to the third region 216. In the fourth region 218 is formed a fifth region (fixed region) 220 having a fixing hole 220a in which a screw 77 to be fixed to the frame 62 is disposed.

The plate-like member 210 is sequentially ridge-folded along the broken lines 232a, 232b, 232c, 232d, and 232e.

First, the tabs 212a and 212b of the first region 212 shown in FIG. 9A and FIG. 9B are ridge-folded along the broken lines 232a and 232b by 180° toward a back surface 240a of the sliding surface 240 described later. The second region 214 is ridge-folded along the broken line 232c by 180° toward the back surface 240a of the sliding surface 240 of the first region 212 and the tabs 212a and 212b.

As shown in FIG. 10A and FIG. 10B, at this time, the surface of the second region 214 that is exposed to the outside becomes a cable holding surface 250 described later. The tabs 212a and 212b are not present on the cable holding surface 250. Therefore, even if the cable 90 is appropriately moved along the cable holding surface 250, the cable 90 does not get caught.

Figure 11A:
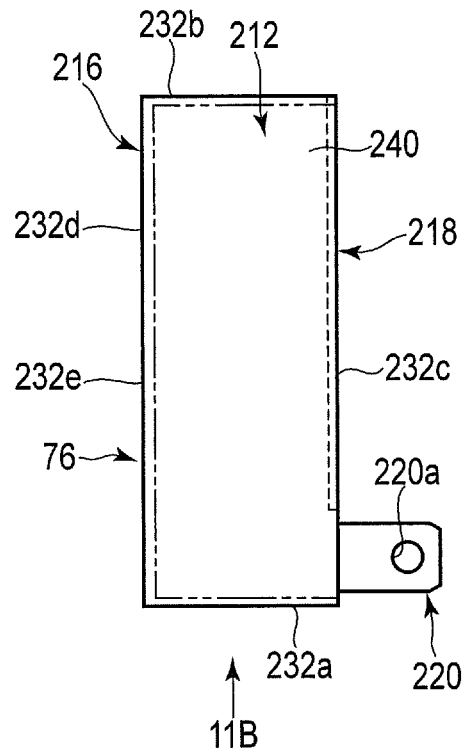
FIG. 11A is a schematic development view of a state in which a remaining part of the broken line of the plate-like member in FIG. 10A is ridge-folded to form a cable holder as observed from a direction of an arrow 11A in FIG. 11B.
Figure 11B:
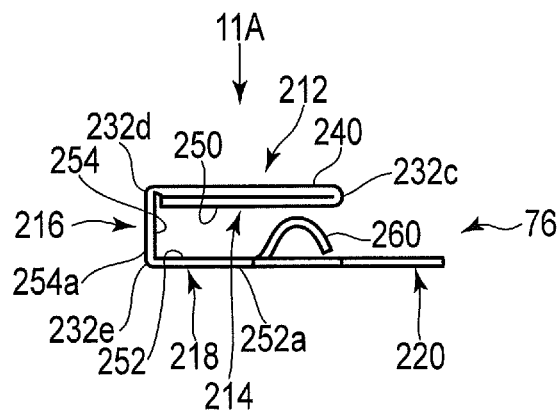
FIG. 11B is a schematic view of the cable holder observed from a direction of an arrow 11B in FIG. 11A.

Then, as shown in FIG. 10A and FIG. 10B, the third region 216 is ridge-folded by 90° along the broken line 232d, and the fourth region 218 is ridge-folded by 90° along the broken line 232e. At this point, a cable retainer 260 having a spring property, and suppressing the cable 90 from protruding outside the cable holder 76 is formed by fixing, such as, by welding, or by cutting and bending. Here, as shown in FIG. 11A and FIG. 11B, even if the cable 90 is appropriately moved along both a facing surface 252 facing the cable holding surface 250 and an adjacent surface 254 adjacent to the cable holding surface 250 and the facing surface 252, the cable 90 would not get caught.

A back surface 252a of the facing surface 252 is disposed on the base plate 73. A back surface 254a of the adjacent surface 254 faces, for example, the cable relay substrate 74.

As shown in FIG. 5, the cable holder 76 is disposed in the second restricting portion 80. In the case of combining the cable holder 76 and the restricting portion 80, the concave portion 190a of the first extending portion 186 and the concave portion 190b of the second extending portion 188 are inserted and fitted between the cable holding surface 250 and the facing surface 252 of the cable holder 76.

The partition 86 and the second restricting portion 80 restrict the movement ranges of the first connection portion 154 and the second connection portion 164 within the range of the sliding surface 240.

Figure 8:
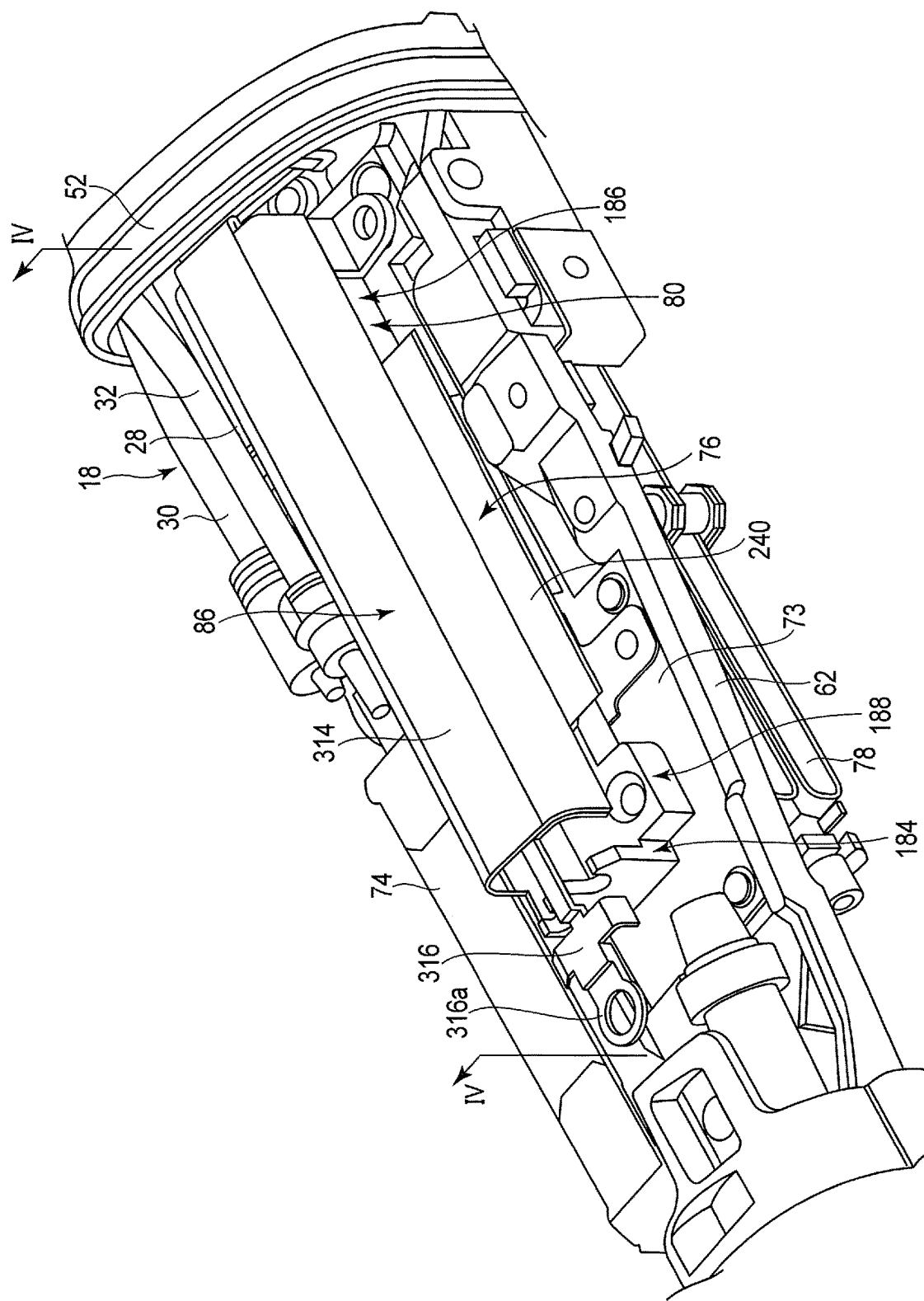
FIG. 8 is a schematic perspective view showing a state in which a partition is disposed with respect to a second restricting portion of the cable holder in FIG. 7, in a state where the first connection portion of the first pulling section and the second connection portion of the second pulling section are disposed on the sliding surface.

As shown in FIG. 8, the partition 86 covers at least a part of the sliding surface 240 of the cable holder 76, the first pulling section 144, and the second pulling section 146. The partition 86 includes the first partitioning member (partition wall) 312 and the second partitioning member (partition wall) 314. The first partitioning member 312 has a substantially U-shaped cross section. The first partitioning member 312 is configured by, for example, a stainless steel alloy material or a hard resin material, which suppresses deformation caused by a load from the outer peripheral side of the first partitioning member 312. Therefore, the first partitioning member 312 cooperates with the sliding surface 240 to form a tunnel-like barrier wall forming a space.

The first partitioning member 312 cooperates with the cable holder 76 and the second restricting portion 80 to restrict a region in which the first connection portion 154 of the first pulling section 144 is movable along the longitudinal axis L. Therefore, the first partitioning member 312 is able to partition the elongated member 18 from the first pulling section 144. The second partitioning member 314 has a substantially U-shaped cross section.

The second partitioning member 314 is configured by, for example, a stainless steel alloy material or a hard resin material, which suppresses deformation caused by a load from the outer peripheral side of the second partitioning member 314. The second partitioning member 314 forms a tunnel-shaped barrier wall that forms a space approximately twice as wide as the first partitioning member 312. The second partitioning member 314 cooperates with the first partitioning member 312, and cooperates with the cable holder 76 and the second restricting portion 80 to restrict a region in which the second connection portion 164 of the second pulling section 146 is movable along the longitudinal axis L. Therefore, the second partitioning member 314 is able to partition the long member 18 from the second pulling section 146, and is able to partition the first pulling section 144 from the second pulling section 146.

The first partitioning member 312 and the second partitioning member 314 are fixed to the frame 62 via the base plate 73 by a common screw 311 (see FIG. 2). As shown in FIG. 2, the partition 86 has a double structure formed by the first partitioning member 312 and the second partitioning member 314, and partitions the first pulling section 144 from the second pulling section 146.

As shown in FIG. 4 and FIG. 12, a support piece 316 is formed integrally on the distal end of the first partitioning member 312. The support piece 316 is fixed to the frame 62 via the base plate 73 by, for example, a screw 317 (see FIG. 4). Here, the support piece 316 maintains the pipe end 174 at the proximal end of the second U-coil pipe 156*b* and the pipe end 178 at the proximal end of the second D-coil pipe 166*b* in a state where they are engaged (supported) at the second engaging portion 184.

The pipe end 172 at the distal end of the first U-coil pipe 156*a* is maintained in a state where it is engaged with (supported by) the first engaging portion 182 by the proximal end of the first partitioning member 312. The pipe end 176 at the distal end of the first D-coil pipe 166*a* is maintained in a state where it is engaged with the first engaging portion 182 by the proximal end of the second partitioning member 314. Therefore, the pipe ends 172 and 176 of the coil pipes 156*a* and 166*a* can be prevented from deviating from the second restricting portion 80.

This allows the first partitioning member 312 and the second partitioning member 314 to protect the first connection portion 154, the second connection portion 164, the wires 152*a*, 152*b*, 162*a*, and 162*b*, and the coil pipes 156*a*, 156*b*, 166*a*, and 166*b*, etc.

As described above, the first partitioning member 312 is formed into a substantially U-shaped cross section. There is no element on the inner peripheral surface of the first partitioning member 312 that would cause the first connection portion 154 to be caught when moving along the longitudinal axis L.

As shown in FIG. 4, the tubular body 154*a* of the first connection portion 154 is set to be movable between the solid line position and the broken line position during use of the endoscope 10. Therefore, the first connection portion 154 is movable at a position where it comes into contact with the sliding surface 240, or within a region on the upper side of the sliding surface 240 shown in FIG. 4.

There is no element on the sliding surface 240 of the cable holder 76 that causes the first connection portion 154 to get caught when moving along the longitudinal axis L. Therefore, the first connection portion 154 is able to move within a predetermined range between the first engaging portion 182 and the second engaging portion 184 in a state of being covered by the first partitioning member 312. Here, the elongated member (built-in object) 18 is disposed at a position adjacent to the first pulling section 144 in the same section P1. However, the first pulling section 144 can be suppressed from interfering with the elongated member 18 when moving.

The second partitioning member 314 is formed into a substantially U-shaped cross section. The first pulling section 144 is separated from the second pulling section 146 by the first partitioning member 312.

There is no element on the sliding surface 240 of the cable holder 76 that causes the second connection portion 164 to get caught when moving along the longitudinal axis L. On the inner peripheral surface of the second partitioning member 314 and the outer peripheral surface of the first partitioning member 312, there is no element that causes the second connection portion 164 to get caught when moving along the longitudinal axis L. Therefore, the second connection portion 164 is capable of moving within a predetermined range between the first engaging portion 182 and the second engaging portion 184 in a state of being covered by the inner peripheral surface of the second partitioning member 314 and the outer peripheral surface of the first partitioning member 312.

Therefore, by using both of the first partitioning member 312 and the second partitioning member 314, the movement of the first pulling section 144 and the second pulling section 146 can be limited without interfering with each other. Here, the elongated member (built-in object) 18 is disposed at a position adjacent to the second pulling section 146 in the same section P1. However, the second pulling section 146 can be suppressed from interfering with the elongated member 18 when moving.

The outer periphery of the second partitioning member 314 has no edge at a portion that abuts the elongated member 18. Therefore, for example, when the operation section 14 is appropriately moved, the elongated member 18 is prevented from getting caught on the outer peripheral surface of the second partitioning member 314, and receiving a load.

Therefore, according to the present embodiment, even if the first pulling section 144 and the second pulling section 146 are disposed in the same first section P1 as the elongated member (built-in object) 18 inside the operation section 14, the endoscope 10 in which the first pulling section 144 and the second pulling section 146 are suppressed from interfering with the elongated member 18 when moving can be provided.

In the present embodiment, an example of fixing the base plate 73 on the frame 62, and further disposing thereon the second restricting portion 80 has been explained. The base plate 73 may or may not be integral with the frame 62. That is, the base plate 73 is not always necessary.

Here, an example of using a part of the cable holder 76 as the sliding surface 240 with respect to the connection portions 154 and 164 of the first pulling section 144 and the second pulling section 146 has been explained. The sliding surface 240 may also be formed by integrating the first extending portion (flat portion) 186 and the second extending portion (flat portion) 188. That is, it is also preferable to form the restricting portion 80 and the cable holder 76 integrally. The restricting portion 80 fixed to the frame 62 may also be formed integrally with the frame 62. In this case, the sliding surface 240 may be integrally formed on the frame 62 itself.

Here, an example of the endoscope 10 having two active bending sections 44 and 46 has been explained. However, the endoscope 10 may also have a structure in which the elongated member (built-in object) 18 is disposed in the same region as the chain end portions 114*a* and 114*b* and the wires 116*a* and 116*b* of the first bending drive assembly 82 of one active bending section 44. In this case, the end portions (pipe ends) 119*a*, 119*b*, 129*a*, and 129*b* of the coil pipes 118*a*, 118*b*, 128*a*, and 128*b* are engaged by the restricting portion 78. Even in this case, the smoothly formed sliding surface 240 and the partition 86 covering the chain end portions 114*a* and 114*b* and the wires 116*a* and 116*b* can suppress interfering with the elongated member (built-in object) 18 when moving the chain end portions 114a and 114b and the wires 116a and 116b.

As shown in FIG. 13, the partition 86 may further have another structure. In the partition 86 shown in FIG. 13, for example, a part of the second partitioning member 314 is cut and bent to form a barrier wall 314a. The barrier wall 314a may be formed at any position of the second partitioning member 314, and may be formed, for example, in the vicinity of the distal end portion, or in the vicinity of the proximal end portion. The barrier wall 314a can partition, for example, the suction tube 28 and the auxiliary water supply tube 34 inside the operation section 14.

Furthermore, depending on the length of the barrier wall 314a extended from the second partitioning member 314, the suction tube 28, the air supply tube 30, and the water supply tube 32 can be partitioned from the auxiliary water supply tube 34. Therefore, when moving the endoscope 10, the movement of the elongated member 18 can be suppressed. In this manner, for example, by limiting the movement of the suction tube 28, the air supply tube 30, and the water supply tube 32, and the movement of the auxiliary water supply tube 34, that is, the movement of the elongated member 18 by the barrier wall 314a, the elongated members (built-in objects) 18 can be prevented from interfering with each other.

By forming the barrier wall 314a in this manner, it is possible to limit the movement of the built-in object of the elongated member 18. Therefore, it is possible to prevent the built-in objects of the elongated member 18 from interfering with each other within a predetermined range.

On the outer surface of the cable holder 76 accommodating the cable 90, there is a sliding surface 240 without irregularities. Therefore, when moving the first connection portion 154 of the first pulling section 144 and the second connection portion 164 of the second pulling section 146 on the sliding surface 240, they are able to travel smoothly in a state where they are prevented from being caught.

By making the first extending portion 186, the second extending portion 188, and the sliding surface 240 of the restricting portion 80 flush, the movements of the first connection portion 154 of the first pulling section 144 and the second connection portion 164 of the second pulling section 146 can be maintained in a smooth state.

In FIG. 2 and FIG. 13, an example of disposing the suction tube 28 in the second section P2 has been explained. However, it is needless to say that the suction tube 28 may also be disposed in the first section P1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion section including a portion to be operated;
an operation section provided on a proximal side of the insertion section, the operation section including a frame extending along a longitudinal axis of the insertion section, the frame separating an inside of the operation section into a first section and a second section;
a first pulling section including:
a first wire disposed inside the operation section, and coupled to the operation section,
a second wire disposed inside the operation section and the insertion section, and coupled to the portion to be operated of the insertion section, and
a connection portion coupling the first wire and the second wire,
the first pulling section being configured to move along an axial direction thereof when transmitting an operation performed by the operation section to the portion to be operated of the insertion section;
a second pulling section disposed inside the operation section, the second pulling section being configured to move along an axial direction thereof when transmitting an operation performed by the operation section to the portion to be operated of the insertion section,
a first elongated member extending inside the operation section;
a restricting portion provided inside the operation section, and configured to restrict a position of the first pulling section;
a sliding surface provided in the restricting portion, and allowing the first pulling section to move along the axial direction; and
a partition covering at least a part of the sliding surface and the first pulling section, the partition being configured to partition the first elongated member and the first pulling section,
wherein
the first pulling section, the first elongated member, the restricting portion, the sliding surface, and the partition are arranged in the first section,
the second pulling section is arranged in the second section, and
the frame is configured to restrict a movement of the first elongated member from the first section to the second section.

2. The endoscope according to claim 1, wherein
the restricting portion includes:
an extending portion provided along a direction in which the first pulling section extends, and
a projecting portion projecting from the extending portion in a direction intersecting a direction in which the first pulling section extends, and
the sliding surface is formed continuously with respect to the extending portion.

3. The endoscope according to claim 2, wherein
the extending portion of the restricting portion is formed into a smooth flat surface, and
the sliding surface is formed flush with the extending portion and smoothly.

4. The endoscope according to claim 1, wherein
at least a part of the first elongated member is provided with a cable inside the operation section,
a conductive holder disposed on the restricting portion, and holding the cable is provided inside the operation section, and
the sliding surface is a part of the holder.

5. The endoscope according to claim 4, wherein
the holder is formed of a conductive plate-like member,
the plate-like member includes:
a first region including the sliding surface and a tab at an end portion of the first region, and
a second region including a cable holding surface that is formed smoothly and prevents the cable from getting caught,
the second region being adjacent to the first region, and the tab of the first region is disposed between a back surface of the sliding surface and a back surface of the cable holding surface.

6. The endoscope according to claim 1,
wherein the sliding surface allows the second pulling section to move along an axial direction together with the first pulling section, and
the partition includes:
  a first partitioning member covering at least a part of the sliding surface and the first pulling section,
    the first partitioning member being configured to partition the first elongated member and the first pulling section, and
  a second partitioning member covering at least a part of the sliding surface and the second pulling section,
    the second partitioning member being configured to partition the first pulling section and the second pulling section, as well as the first elongated member and the second pulling section.

7. The endoscope according to claim 1, wherein the partition includes a barrier wall configured to partition a second elongated member that is different from the first elongated member.

8. The endoscope according to claim 1, wherein
the operation section includes a first coil pipe through which the first wire is inserted,
the insertion section includes a second coil pipe through which the second wire is inserted,
the restricting portion includes a first engaging portion and a second engaging portion that are spaced apart from each other,
  the first engaging portion being configured to engage with an end portion of the first coil pipe, and
  the second engaging portion being configured to engage with an end portion of the second coil pipe,
the first engaging portion and the second engaging portion are configured to maintain a state in which the end portion of the first coil pipe and the end portion of the second coil pipe face each other,
  the first engaging portion and the second engaging portion being spaced apart from each other, and
the connection portion is movable in a range of a region formed by the partition and the sliding surface, the connection portion being partitioned with respect to the elongated member by the partition.

9. The endoscope according to claim 8, wherein the partition is configured to maintain:
  a state in which the end portion of the first coil pipe is supported by the first engaging portion, and
  a state in which the end portion of the second coil pipe is supported by the second engaging portion.

10. The endoscope according to claim 1, wherein the portion to be operated of the insertion section includes:
  a first bending section disposed near a distal end portion of the insertion section, and
  a second bending section disposed at a proximal side of the first bending section, and to which a distal end of the first pulling section is coupled.

11. The endoscope according to claim 10, wherein the operation section includes:
  a first operation section that is operated when the first bending section is being bent, and
  a second operation section that is operated when the second bending section is being bent,
when transmitting a driving force by an operation of the first operation section to the first bending section of the insertion section, a moving member that moves along an axial direction thereof is inserted through the operation section and the insertion section,
the operation section includes:
a grip; and
the frame is configured to separate a region in which the moving member is disposed and a region in which the first pulling section is disposed in cooperation with the grip.

12. The endoscope according to claim 11, wherein
the frame is formed plate-like, and
the region in which the moving member is disposed and the region in which the first pulling section is disposed are on opposite sides of the frame.

13. The endoscope according to claim 1, wherein the first elongated member is selected from a group comprising an illumination optical system, an observation optical system, a treatment instrument insertion channel, a suction tube, an air supply tube, a water supply tube and an auxiliary water supply tube.

14. The endoscope according to claim 1, wherein
the portion to be operated of the insertion section includes
  a first bending section which is disposed near a distal end portion of the insertion section, and to which a distal end of the second pulling section is coupled, the first bending section being configured to be actively bent by an operation of the operation section, and
  a second bending section which is disposed at a proximal side of the first bending section, and to which a distal end of the first pulling section is coupled, the second bending section being configured to be actively bent by the operation of the operation section.

15. The endoscope according to claim 1, wherein in the first section, the partition includes:
  a first partitioning member covering at least a part of the sliding surface and the first pulling section, the first partitioning member being configured to partition the first elongated member and the first pulling section, and
  a second partitioning member covering at least a part of the first partitioning member, the sliding surface and the second pulling section,
the second partitioning member being configured to partition the first pulling section and the second pulling section, as well as the first elongated member and the second pulling section, and
the first elongated member is provided in the first section on a side of the second pulling member with respect to the second partitioning member.

* * * * *